United States Patent [19]

Stover

[11] Patent Number: 5,228,995
[45] Date of Patent: Jul. 20, 1993

[54] BIOCHEMICALLY ENHANCED HYBRID ANAEROBIC REACTOR

[76] Inventor: Enos L. Stover, Rte. 4, Box 666, Stillwater, Okla. 74074

[21] Appl. No.: 872,444

[22] Filed: Apr. 23, 1992

[51] Int. Cl.$^5$ .............................................. C02F 3/28
[52] U.S. Cl. .................................. 210/603; 210/607; 210/610; 210/615; 210/631; 210/150; 210/180; 210/194; 210/218; 210/917
[58] Field of Search .............. 210/603, 607, 608, 610, 210/612, 615, 631, 150, 151, 180, 194, 196, 209, 218, 220, 299, 312, 917

[56] References Cited

U.S. PATENT DOCUMENTS

| | | | |
|---|---|---|---|
| 3,371,033 | 2/1968 | Simmons et al. | 210/151 |
| 4,067,801 | 1/1978 | Ishida et al. | 210/603 |
| 4,134,830 | 1/1979 | Skogman et al. | 210/603 |
| 4,311,593 | 1/1982 | Benjes et al. | 210/603 |
| 4,315,823 | 2/1982 | Witt et al. | 210/605 |
| 4,322,296 | 3/1982 | Fan et al. | 210/610 |
| 4,491,522 | 1/1985 | Ishida et al. | 210/603 |
| 4,530,762 | 7/1985 | Love | 210/603 |
| 4,561,974 | 12/1985 | Bernard et al. | 210/151 |
| 4,582,600 | 4/1986 | Atkinson et al. | 210/151 |
| 4,632,758 | 12/1986 | Whittle | 210/603 |
| 4,676,906 | 6/1987 | Crawford et al. | 210/603 |
| 4,735,723 | 4/1988 | Mulder | 210/603 |
| 4,796,433 | 5/1988 | Nöbl et al. | 210/603 |
| 4,826,600 | 5/1989 | Ely et al. | 210/603 |
| 4,846,289 | 7/1989 | Jeris et al. | 210/610 |
| 4,919,815 | 4/1990 | Copa et al. | 210/603 |
| 4,940,546 | 7/1990 | Vogelpohl et al. | 210/613 |
| 4,948,509 | 8/1990 | Stack | 210/603 |
| 5,006,249 | 4/1991 | Green et al. | 210/603 |

*Primary Examiner*—Christopher Upton
*Attorney, Agent, or Firm*—Dougherty, Hessin, Beavers & Gilbert

[57] ABSTRACT

A biochemically enhanced hybrid anaerobic reactor (BEHAR) system has been developed for treatment of high strength industrial wastewaters. The process is designed and operated based on specific criteria developed around critical biochemical and microbiological principles of the facultative and anaerobic microorganisms involved in anaerobic treatment. Biological kinetic relationships developed by the inventor for substrate removal, methane gas production, and biogas quality control as a function of the mass substrate loading rate are used for designing and operating the BEHAR process. A specific formulation of biological growth micronutrients has been developed for enhancing the anaerobic treatment process. Ferric chloride, one of the chemicals used as a micronutrient, is also utilized for sulfide toxicity control, biogas cleaning without scrubbing, and odor control. Magnesium hydroxide is also used as a micronutrient while offering the added benefits of sulfide toxicity control, biogas cleaning without scrubbing, odor control, and addition of alkalinity and buffering capacity to the BEHAR system, along with sodium toxicity control. Various combinations of ferric or ferrous salts and magnesium hydroxide are used to provide maximum and optimized bulk liquid sulfide control and biogas $H_2S$ control. Heavy metal toxicity control is also provided in problematic wastewaters by the addition of sulfates which are reduced to sulfides to precipitate heavy metals as insoluble metal sulfides. An understanding of these kinetic, microbiological and biochemical principles combined with a unique reactor design to enhance the practical application of these principles constitutes the BEHAR process.

18 Claims, 3 Drawing Sheets

BIOCHEMICALLY ENHANCED HYBRID ANAEROBIC REACTOR

BACKGROUND OF THE INVENTION

1. Field of the Invention

The invention relates generally to anaerobic processing of waste material and, more particularly, but not by way of limitation, to use of a biochemically enhanced hybrid anaerobic reactor (BEHAR) for processing of such as high strength industrial waste waters.

2. Description of the Prior Art

Treatment of waste by either aerobic or anaerobic processing is quite old and various types and sizes of digester have been developed for use in such systems. More recent developments have seen construction of more specific types of digester that are designed for clean-up of wastewater containing various impurities. U.S. Pat. No. 4,311,593 discloses a digester system for use with wastewater that is effluent from molasses fermentation processing. The wastewater is treated in an anaerobic vessel which includes high surface area media. The wastewater is directed downwardly through the media for interaction with microorganism biomass with production of methane while reducing oxygen demand of such material. Various nutrients may be added to the mixture in order to promote growth of the microorganisms. The sloughed biomass is recirculated from the bottom of the digester to the top thereof while the methane stream is selectively recirculated into the bottom of the digester and bubbled up through the media and wastewater therein. Preferably a nominal pressure is maintained on the digester to urge carbon dioxide produced in the process to remain in solution with the effluent.

U.S. Pat. No. 4,530,762 teaches an anaerobic reactor for wastewater treatment. The tank apparatus includes a reaction hood in a lower extremity that defines a mixing zone where influent water mixes with liquid and biological solids already in the zone beneath the hood. The reaction tank may include a fixed film media above the hood enclosure and the system utilizes a sludge thickener for concentrating the sludge removed from the tank. This anaerobic treatment process may be described as three distinct steps (A) acid fermentation, (B) acid regression, and (C) alkaline fermentation. U.S. Pat. No. 4,632,758 discloses yet another anaerobic treatment system wherein wastewater to be treated is introduced into the bottom of the reactor and forced upward over media surfaces wherein the waste is consumed by anaerobic digestion with usual by-product of methane and a biological sludge. Methane given off as a by-product of the anaerobic digestion may be used as a source of fuel for heating the reactor influent immediately before it is introduced into the reactor. Still further, the reactor effluent may be directed to a degassifier whereby entrained gas is released before introducing the degassified reactor effluent into a clarifier whereby the effluent's biological sludge will settle out. An alkaline substance such as bicarbonate may also be introduced to form a bicarbonate slurry in an amount sufficient to enhance the activity of the methane producing bacteria, but insufficient to effect directly the pH of the reactor contents.

SUMMARY OF THE INVENTION

The anaerobic reactor is a "hybrid" upflow suspended growth/fixed film system. The anaerobic reactor has three distinct zones. The bottom half of the tank is the suspended growth zone where, as the name implies, the biological mass is kept in suspension by a combination of the upward flow of the wastewater and recycled effluent, and the upward movement of the byproduct biogas. The reactor recycled effluent can vary from zero to ten times the forward flow rate, as needed to maintain the desired hydraulic regime in the reactor.

Half way up the tank there is a structural steel support system to support the thick pack of filter media. The filter media provides a surface for the attachment of a biological slime which forms the fixed-film zone of the reactor. The media is corrugated crossflow type or a combination of vertical flow and crossflow media, similar to that used in trickling filter systems. The crossflow media provides solids/liquid/gas separation required to maintain a high solids inventory in the system or a high solids retention time.

When the tank is full of liquid, buoyant effects help support the media. However, when the tank is drained for maintenance or repairs, the heavy biological growth will put a significant load on the support system. Therefore, the support system is designed to resist these "worst case" loads.

Above the media is a third zone of relatively clear liquid in a quiescent or clear zone. The treated effluent is removed at this quiescent zone by a system of submerged pipes. To ensure uniform flow distribution across the entire cross sectional area of the tank, the influent distributor system and effluent collection system are designed to cover the bottom and top of the tank to the greatest extent possible. Treated wastewater collected by the effluent collection piping is discharged to a chamber located on the side of the anaerobic reactor.

Even though the reactor vessel is normally insulated, there will usually be a need to add heat, especially in the winter, in order to maintain the optimum temperature in the reactor. Final temperature control is normally achieved by adding heat to the recycle stream using heat recovered from combustion of the biogas. The heat from the biogas burner is utilized to satisfy the baseload heating requirements of the system, and a simple thermostatic valve and shunt system is used to maintain the recycle flow at a constant temperature.

For reaction enhancement, a simple steam injector system, controlled by a temperature controller on the combined influent/recycle line, is used for "trim" temperature adjustments and to supplement the stack heat recovery system during periods of very cold weather and/or when the production of biogas is insufficient to satisfy the heating needs of the system. A spray water system is provided to break up the scum and facilitate its removal by scum removal draw off piping. A portion of the recycle stream is split off and used for the spray water system. Scum is removed continuously via a floating decanter to the effluent box to be discharged with the reactor effluent. No pH adjustment of the wastewater is made prior to mixing with the recycle flow in order to make beneficial use of the alkalinity and buffering capacity of the recycle stream. Magnesium hydroxide, lime, and caustic can be added for alkalinity addition to the system. $Mg(OH)_2$ is fed at a preset feed rate in order to provide micronutrient magnesium, baseload alkalinity addition, and sulfide toxicity control. The automatic pH controller is then used to add lime or caustic as needed for alkalinity addition for final pH trim control.

Normally, for enhancing operation, six separate chemical feed systems are provided to feed $Mg(OH)_2$, NaOH, lime, $FeCl_3$, macronutrients and micronutrients. As previously described, $Mg(OH)_2$ and NaOH are added to provide alkalinity, magnesium as a micronutrient, and for sulfide complexation. $Mg(OH)_2$ is added as the primary alkalinity source under conditions where excessive alkalinity requirements are needed in order to minimize potential for sodium toxicity in the reactor. Lime also provides alkalinity and calcium as a micronutrient. $FeCl_3$ is added as a micronutrient, for odor control, and for sulfide complexation. Both macronutrients (nitrogen and phosphorus) and micronutrients (trace metals) are critical to successful performance of anaerobic treatment systems. These chemicals are added based on chemical analyses of the wastewater and treated effluent from the BEHAR reactor.

Therefore, it is an object of the present invention to develop an optimized hybrid anaerobic reactor process for the treatment of high strength industrial wastewaters.

It is also an object of the invention to employ certain anaerobic kinetic relationships for optimization of anaerobic bacterial growth, substrate removal, biogas production, and resistance to inhibitory or toxic environmental conditions.

It is yet another object of the invention to provide an anaerobic reaction process having the capability for biogas hydrogen sulfide cleaning within the reactor based upon the combined use of a balanced mixture of magnesium hydroxide and iron salts.

Finally, it is an object to provide method and apparatus for effecting continuous and more complete clean-up of particularly foul waste water.

Other objects and advantages of the invention will be evident from the following detailed description when read in conjunction with the accompanying drawings which illustrate the invention.

DETAILED DESCRIPTION OF THE INVENTION

The anaerobic treatment process produces a methane rich biogas as a byproduct of the treatment process. The biogas consists primarily of methane ($CH_4$), carbon dioxide ($CO_2$), and hydrogen sulfide ($H_2S$). The $H_2S$ in the biogas, if not controlled, can cause severe odor problems and biological toxicity. Furthermore, $H_2S$ is an extremely corrosive gas and can be lethal in high concentrations.

High concentrations of $H_2S$ in the biogas are normally the result of the presence of high sulfate concentrations in the wastewaters entering the treatment system. The sulfate in the influent wastewater can be a major concern with anaerobic pretreatment. The sulfate will be reduced to sulfides in the anaerobic treatment system which, in high concentrations, can inhibit the biological process in addition to creating serious odor problems. The sulfides in the reactor may be present in soluble or insoluble form, depending on the cations with which they are associated. The soluble sulfide forms a weak acid which ionizes in aqueous solution, the extent depending upon the pH. Thus, it is possible to have $H_2S$, $HS^-$, and $S^=$ in solution. Because of the limited solubility of hydrogen sulfide, a certain portion of the hydrogen sulfide formed will escape with the biogas produced. The quantity of hydrogen sulfide escaping with the biogas is related to the rate of production of biogas by the treatment process, as well as the relationship with aqueous soluble sulfide. The sulfide solubility in the reactor bulk liquid will decrease with decrease in reactor pH, allowing more sulfides in the form of $H_2S$ to escape in the biogas produced. In other words, $H_2S$ in the biogas increases with decrease in reactor operating pH.

By precipitating the sulfides in the bulk liquid and reducing the soluble sulfides, the driving force for sulfide stripping in the biogas is reduced, and the biogas sulfide content is reduced. Ferric chloride has typically been added to anaerobic systems to precipitate sulfides. However, controlling the sulfur in the anaerobic reactor by ferric chloride precipitation can be difficult. The quantity of ferric chloride required at high sulfide concentrations can reduce the reactor liquid pH which in turn increases the caustic requirement to maintain the optimum pH for the anaerobic process. The increased chemical requirements would not only dramatically increase the cost of operation of the system, but could cause operational problems as well. Sodium concentrations in the anaerobic reactor beyond a certain threshold level can also be inhibitory to the treatment process when sodium hydroxide is used to combat the acidity additions with ferric chloride.

Microorganisms

The anaerobic degradation of organic matter to methane involves a complex interaction of three groups of bacteria. The first group of bacteria is the fermentative (or facultative) bacteria, which hydrolyzes complex long chain organics and ferments them to fatty acids, alcohols, and other soluble organics. The second group of bacteria, the acetogenic bacteria, has been found to degrade propionic acid and longer chain fatty acids to acetate, $H_2$, and $CO_2$. The third and final group of bacteria, the methanogens, is the most critical bacteria of the three groups since most of the conversion of soluble organics to methane (an insoluble gas) is by these bacteria. The methanogens are considered to be the rate limiting step in anaerobic treatment, and an upset condition is usually accompanied by an increase in volatile acids, and a decrease in process efficiency. Overall, anaerobic treatment can result in over 90% of the organic waste being converted to methane.

Facultative bacteria are among the largest group of bacteria in nature. These bacteria can function either in an aerobic or anaerobic environment. The most common group of facultative bacteria is the Pseudomonas. Additional common facultative bacteria that have been identified in wastewater treatment systems include Alcaligenes, Achromobacter, Flavobacterium and various enteric bacteria.

The obligate anaerobic bacteria, which includes the methanogens, cannot tolerate dissolved oxygen. Clostridium is the major group of strict anaerobes. Sulfate reducing bacteria are also strict anaerobes that belong to Desulfovibrio. They can metabolize a wide variety of organic compounds while reducing sulfates to various reduced sulfur intermediates, including hydrogen sulfide. The methane bacteria are also strict anaerobes that require a highly reduced environment for metabolism. They include Methanobacterium, Methanosarcina, and Methanococcus. Certain methane bacteria reduce carbon dioxide with hydrogen to produce methane and water while others metabolize acetate. There is strong competition between the methane bacteria and the sulfate reducers.

Sulfate Reduction

Desulfovibrio bacteria can use sulfates as their primary source of electron acceptors. The electron changes produce a series of reduced sulfur compounds, starting with thiosulfates and working through sulfur to sulfides. Energy transfer determines the changes in the sulfates. In the presence of excess organic matter that is readily metabolized by the Desulfovibrio bacteria, the reduction reactions readily proceed to sulfides as shown:

$$\text{Organic Matter} + SO_4 \rightarrow H_2S + CO_2 \quad (1)$$

The reduction of sulfate produces an increase in pH in the reactor bulk liquid. The hydrogen sulfide is partially soluble and insoluble. As hydrogen sulfide is produced above its solubility level it diffuses out of solution into the gases in proportion to its solubility. Hydrogen sulfide is a weak acid and will act as a buffer in the bulk liquid.

At a pressure of 1.0 atmosphere and a temperature of 35° C., hydrogen sulfide is soluble to a maximum level of 2,750 mg/l at pH 4.0. However, biological systems operate at pH values around 7.0, and as the pH increases above 4.0, hydrogen sulfide forms hydrogen bisulfide as shown:

$$H_2S \rightarrow HS^- + H^+ \quad (2)$$

At pH 7.0 there will be approximately a 50:50 split with a total allowable sulfide concentration of 5,765 mg/l ($H_2S + HS^-$). Formation of bisulfide therefore allows more sulfides to remain in solution. Since hydrogen sulfide is the culprit creating toxicity in anaerobic treatment, the toxicity can be reduced by raising the pH above 7.0 to drive the reaction toward bisulfide. By maintaining hydrogen sulfide levels below 200 mg/l, toxicity problems can be eliminated.

Relative concentrations of electron donors (organic matter) and sulfates controls the end product formation. If the sulfate concentration is higher than the organic matter available for metabolism, the sulfate reducers do not have enough electrons to completely reduce the sulfates to sulfides. The overall reduction process can be expected to follow the pattern shown:

$$\text{Organic Matter} + SO_4 \rightarrow [SO_3 - SO_2 - S_2O_3 - S_2 - HS - S] + CO_2 \quad (3)$$

The thiosulfates are readily soluble, whereas the free sulfur is insoluble.

Environmental Conditions

Primary environmental factors of concern include maintaining optimum temperatures of 80° to 100° F. for mesophilic conditions and 120° to 130° F. for thermophilic conditions, a pH range of 6.5 to 7.5 supplying adequate macronutrients and micronutrients, and minimizing and/or controlling toxic organic or inorganic compounds. Certain trace inorganic nutrients and vitamins are needed in anaerobic treatment processes. Trace metals such as nickel, iron, cobalt, molybdenum, selenium and tungsten are stimulatory to methanogens at low concentrations. It is extremely important to monitor and control these parameters during start-up and operations of anaerobic reactors. In addition, adequate amounts of calcium and magnesium are required to promote the growth of sludge granules which are prevalent in the BEHAR process.

The most effective indicators of performance are pH, volatile acid to alkalinity ratio, and gas (methane) production. The key to successful start-up is to increase the biological solids inventory by gradual increases in the flow and organic loading to the plant. It is critical that the loadings are increased in proportion to the biomass in order to control the food-to-microorganism (F/M) ratio. This aspect of both plant start-up and stabilized plant operations can be monitored by the system pH, volatile fatty acids, volatile fatty acid/alkalinity ratio, COD removal efficiency, methane content of the gas, and reactor temperature. Adjustments are required when any of these parameters exceed pre-set acceptable operating ranges.

Generally, the volatile acid/alkalinity ratio should be maintained at less than 1.0 in order to obtain optimum system performance. When this ratio exceeds 1.0, immediate corrective action(s) should be taken, otherwise, the volatile acids will cause a drop in the pH and the methanogen activity will decrease. The methane production is a direct measure of the metabolic activity of the methanogenic bacteria, and as such, has great potential as a diagnostic tool of anaerobic activity. The use of pH alone is not as sensitive an indicator of reactor activity because environmental changes will already have taken place before a pH change is noticed. However, knowledge of the pH is important to good operation of the system and should be maintained at approximately 6.5 to 7.5 for most applications.

Anaerobic Treatment Kinetics

The key to successful design and operation of the present BEHAR system is matching the number of microorganisms in the system to the organic substrate loading rate of the system, or controlling the F/M ratio. Accurate prediction and modeling of both treatment performance and methane production has been accomplished when substrate utilization and methane production were expressed as functions of the mass substrate loading ratio (F/M) by monomolecular kinetics for both suspended growth and fixed-film systems. Extensive evaluation of anaerobic reactors in recent testing has shown that these systems comply with the same types of kinetic relationships previously developed for description of aerobic suspended growth and fixed-film reactors.

Extensive studies with anaerobic biological reactors by the inventor have shown that the relationships of substrate removal versus substrate applied were applicable to anaerobic systems. This analysis has allowed the development of mathematical models based on the experimental determination of biological kinetic constants describing substrate removal to be applied to anaerobic system design and operation. A second very important observation has also been made relative to both methane gas production and quality. Not only was substrate removal found to be a function of substrate loading in anaerobic systems, but both the gas production and gas quality were also observed to be dependent on the substrate loading. The total gas production rate and methane quality can also be mathematically modeled and accurately predicted in a similar manner to substrate removal. The gas production and quality are both dependent on the amount of substrate removed, and both gas production and substrate removal depend on the total substrate loading rate. The mathematical models and application methodology, along with data from bench scale, pilot scale and full scale operating systems have been presented in the inventor's publications. These models are used for the design and operation of the BEHAR anaerobic systems described herein. The kinetics of substrate removal, methane gas production and gas quality have all been found to be dependent and predictable as a function of the mass substrate loading or application rate.

When considering the BEHAR reactor volume, a mass balance of substrate into and out of the reactor volume can be made as follows:

$$\text{Mass of substrate into the reactor} = \text{Mass of substrate out of the reactor} + \text{Mass of substrate consumed biologically}$$

In the case of the BEHAR reactor, the reactor volume is expressed in million gallons or cubic meters with the resultant mass balance equation:

$$FS_i = FS_e + \frac{(dS)}{(dt)_G} V \qquad (4)$$

where:
F = flow rate, MGD (m³/day)
$S_i$ = influent substrate concentration, mg/l
$S_c$ = effluent substrate concentration, mg/l
V = reactor volume in million gallons (cubic meters)

$\frac{(dS)}{(dt)_G}$ = specific substrate utilization rate, lbs/1,000 ft³/day (Kg/m³/day)

Mathematical description of this substrate utilization rate as a function of the substrate loading rate or F/M ratio based on monomolecular kinetics follows:

$$\frac{(dS)}{(dt)_G} = \frac{U_{max} \frac{FS_i}{V}}{K_B + \frac{FS_i}{V}} \qquad (5)$$

where:

$\frac{FS_i}{V}$ = mass loading rate, lbs/1,000 ft³/day (Kg/m³/day)

U = specific substrate utilization rate, lbs/1,000 ft³/day (Kg/m³/day)
$U_{max}$ = maximum specific substrate utilization rate, lbs/1,000 ft³/day (Kg/m³/day)
$K_B$ = proportionality constant or substrate loading at which the rate of substrate utilization is one-half the maximum rate, lbs/1000 ft³/day (Kg/m³/day)

Substitution of Equation (5) into Equation (4) and solving for the reactor volume, V or the effluent quality, $S_c$, provides the design equation or the effluent quality predictive equation to be used for operation, respectively. The kinetic constants, $U_{max}$ and $K_B$, are determined experimentally. The specific substrate utilization rate (U) is plotted as a function of the specific substrate loading rate or mass substrate loading rate. Then the reciprocal of U is plotted as a function of the reciprocal of the mass loading rates. $U_{max}$ is the reciprocal of the Y-axis intercept, and the slope of the line is equal to $K_B/U_{max}$.

Figure 1:
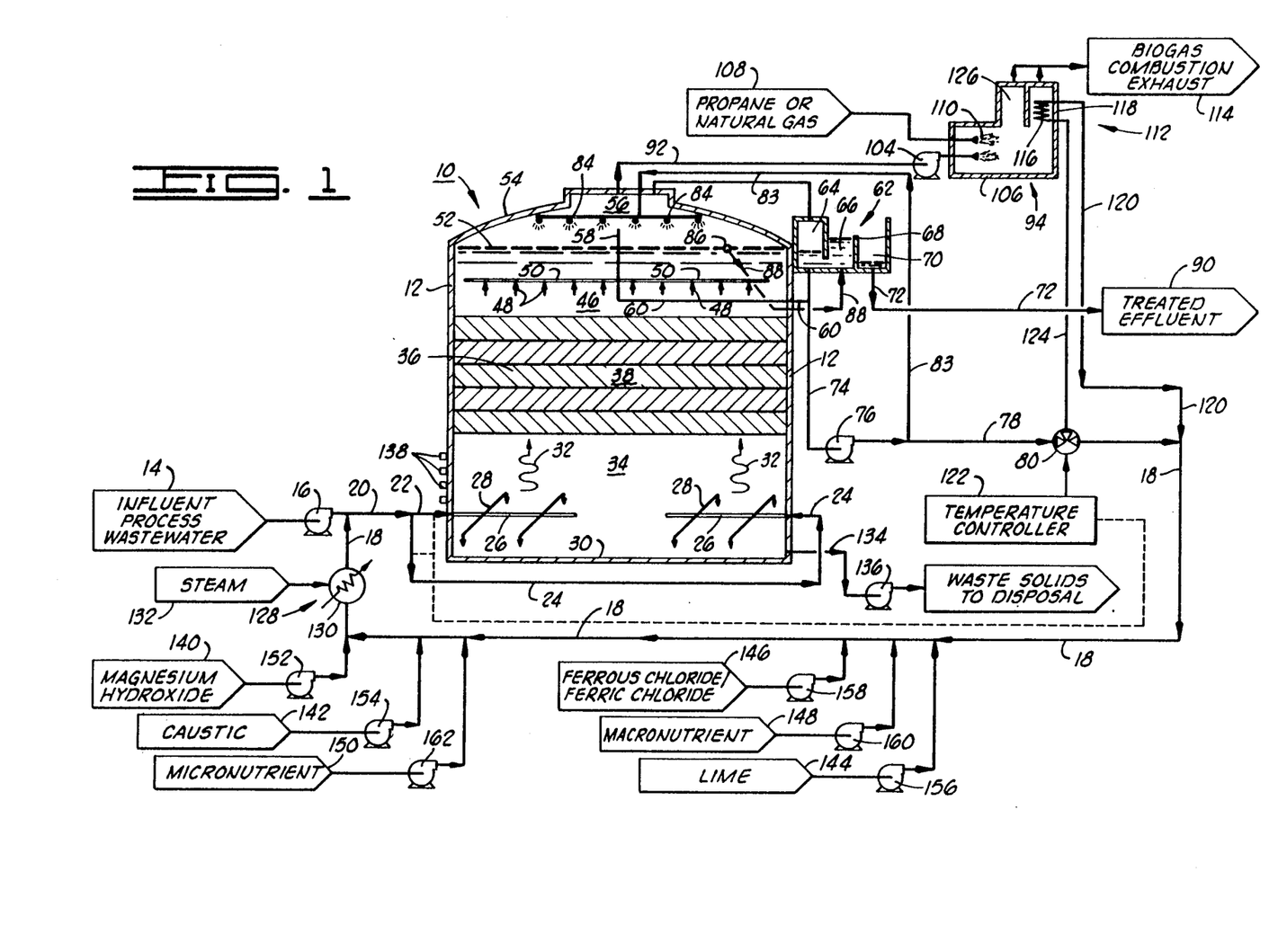
FIG. 1 is a schematic diagram of one embodiment of the Biochemically Enhanced Anaerobic Reactor process in which the process consists of a single, large reactor vessel.
Figure 2:
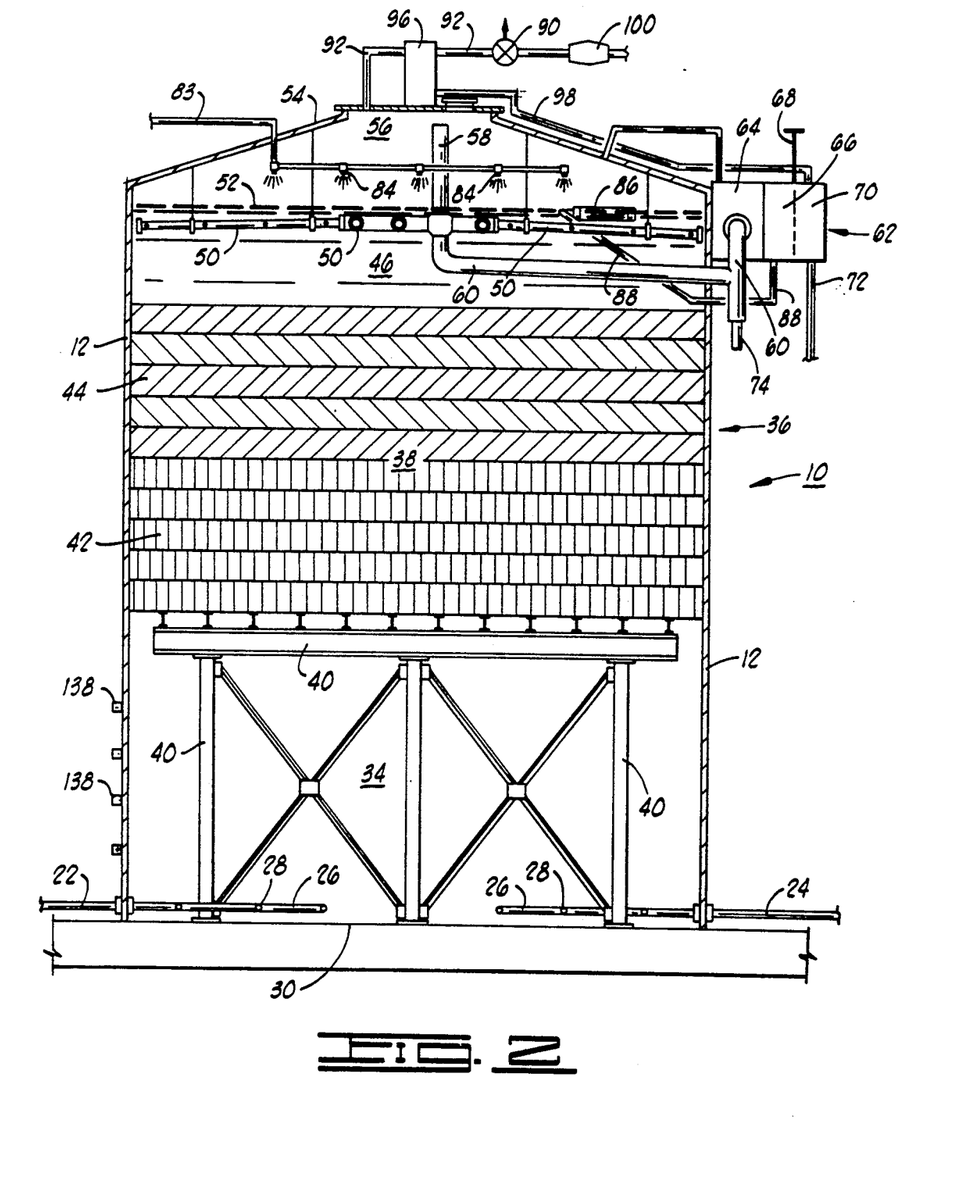
FIG. 2 is a cross sectional view of the reactor in greater detail taken along line 2—2 of FIG. 3.

FIG. 1 illustrates the system for treating wastewater according to the present invention. The main component is the anaerobic reactor 10 with tank 12. A source 14 designates the wastewater to be treated by the process which may be any wastewater solution having organic and/or other contaminants suitable for anaerobic treatment. The fluid is pumped to the reactor 10 by an influent pumping system 16, is mixed with recycled effluent from the anaerobic reactor on recycle line 18 and conveyed to the reactor 10 through conduit 20 and one or more influent pipes 22, 24 which enter the reactor 10 at the bottom. See also FIGS. 2 and 5. The flow of influent fluid and recycled effluent is distributed by a system of influent distributor pipes 26, 28 along the reactor floor so as to evenly distribute the flow across the entire area of the reactor 10. The influent distributor pipes 26, 28 are perforated at intervals along their length which results in the wastewater fluid and recycled reactor effluent on recycle line 18 exiting the distributor piping 26, 28 at high velocity thereby to impart mixing energy to the contents of the tank to prevent settling of the biological solids within the reactor 10.

Figures 3, 4, 5:
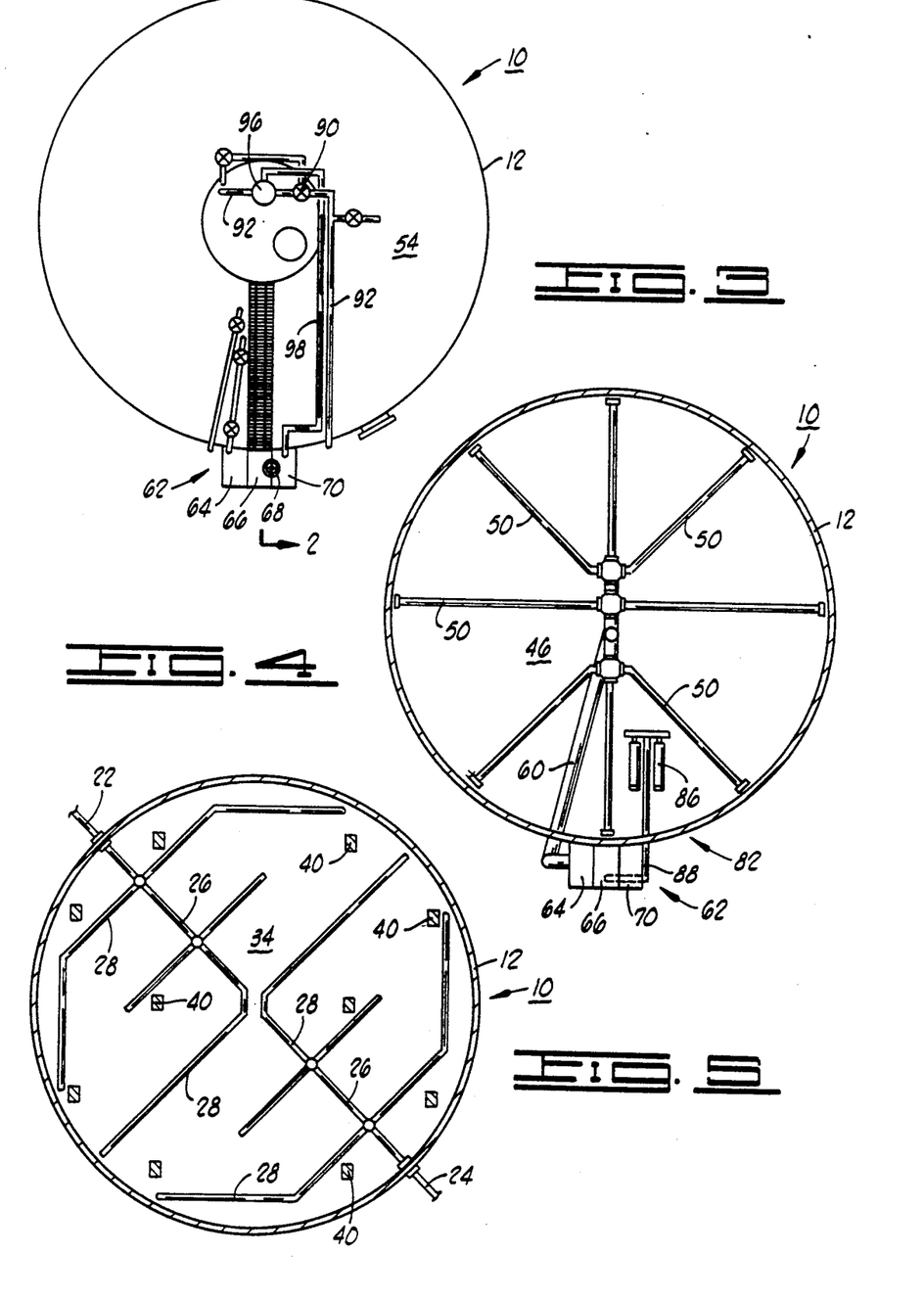
FIG. 3 is a top plan view of the reactor tank roof containing one possible arrangement of the piping associated therewith.
FIG. 4 is a horizontal cross-sectional view of the reactor showing one possible arrangement for the effluent draw-off piping and scum/foam removal piping in the quiescent zone.
FIG. 5 is a horizontal cross-sectional view taken at the bottom of the reactor tank containing one possible arrangement for the influent distributor piping associated therewith.

The influent distributor pipes 26, 28 are valved to allow isolation of areas of the distributor to force all of the flow through a portion of the distributor to help prevent the accumulation of deposits in the pipes and orifices and to agitate the tank to prevent packing of sludge at the bottom floor 30 of the reactor. The wastewater fluid and recycled effluent assumes a vertical flow path 32 upon entering the reactor 10 and mixes with the biological solids in the suspended growth zone 34. The biological solids are maintained in suspension in the suspended growth zone 34 by a combination of the upward flow 32 of the fluid and the upward movement of the byproduct biogas.

Above the floor 30 of the reactor 10 there is a thick pack of PVC filter media 36 which provides surface area for the attachment of biological slime. This forms the fixed film zone 38 of the reactor 10. The layered media 36 is supported on a media support structure 40 (FIG. 2) which may consist of such as a lattice work of structural steel members or other construction suitable to withstand the structural loads imparted by the media pack 36. The layered media pack 36 may be corrugated PVC sheet type and may be crossflow construction or vertical construction, or a combination of both. Typically, the lower portion of the media pack 36 is vertical flow type 42 (FIG. 2) which tends to resist clogging better in high rate loading applications. The upper portion of the media pack 36 is typically a crossflow type 44 construction which provides solids/liquid/gas separation required to maintain high solids inventory in the reactor, i.e., a high solids retention time.

Above the media pack 36 is a volume of relatively clear liquid referred to as the quiescent zone 46 where the treated effluent 48 from the reactor 10 is removed by the effluent collection piping system 50 which is arranged to collect the effluent evenly from across the entire cross-sectional area of the reactor 10. See also FIGS. 2 and 4. Byproduct biogas is collected in the headspace above the water line 52 and below the roof 54 of the reactor 10 and is referred to as the biogas storage zone 56. The reactor tank 12 is air-tight to prevent the entrance of air into the reactor 10 and to prevent the escape of biogas into the atmosphere. The effluent collection system piping 50 is vented into the biogas storage zone 56 by a gas vent line 58 to prevent the accumulation of biogas in the effluent collection piping 50. The reactor effluent is removed from the reactor 10 through the effluent draw-off line 60 to the effluent control system 62. The effluent control 62 is divided into three chambers. Effluent control chamber 64 is closed to the atmosphere, and serves as the water seal to prevent the escape of biogas from the reactor 10. Effluent control chamber 66 is open to the atmosphere and is equipped with an adjustable weir 68 to control the water surface elevation inside the reactor 10 as well as to maintain a positive pressure on the biogas inside the reactor 10. The treated effluent from the anaerobic treatment process is then conveyed from an effluent control chamber 70 via the treated effluent line 72.

A portion of the treated effluent is split off from the forward flow line 60 prior to entering the effluent control chamber 64 to be recycled on line 74 back to the recycle line 18 and influent line 20 to the anaerobic reactor 10. The recycle flow on line 74 is pumped back to the influent piping 20 by the recycle pump 76 via the internal recycle line 78, control valve 80, and recycle line 18. As mentioned previously, the internal recycle flow rate is designed to provide the optimum hydraulic throughput rate to maintain the biological solids in the suspended growth zone 34 in suspension. The internal recycle flow rate can be varied from 0 to 10 times the forward flow rate to maintain the desired hydraulic flow regime in the reactor. The recycle pump system 76 typically consists of two or more pumps to allow flexibility in operation. In addition, the pumps may be controlled by a timer to cause the spare recycle pump to operate intermittently to increase the recycle flow rate thereby to enhance the cleaning and mixing effects at the influent distributor pipes 26, 28.

It is characteristic of anaerobic treatment reactors that as the byproduct biogas rises to the top of the tank into the biogas storage zone 56, some solids are carried to the water surface 52 to form a layer of scum. Left to accumulate, the scum can become a hardened crust which can restrict the transfer of biogas from the liquid. To counter these effects, the process is equipped with a floating foam/scum control system 82 (FIG. 4) which utilizes a portion of the internal recycle flow on conduit 83 for antifoam spray water. The spray water is applied as a coarse spray water onto the water surface 52 to break up the scum by a number of spray nozzles 84 located near the roof 54 of the reactor. The scum is removed by a floating skimmer 86 and is conveyed to the effluent control chamber 66 via the scum removal line 88 where it is discharged on line 72 with the treated effluent 90.

Biogas generated by the anaerobic treatment process is collected in the biogas storage zone 56. Biogas pressure above a predetermined set point is vented from the reactor 10 by an automatic pressure regulating/relief valve 90 in biogas removal line 92. See also FIG. 3. The vented biogas is conveyed from the reactor 10 to a biogas burner system 94 via the removal line 92. The biogas removal line 92 is equipped with a drip trap 96 to remove some of the moisture from the saturated gas prior to combustion. Condensate collected in the drip trap 96 is drained to the effluent control chamber 70 via a condensate drain line 98. A flame arrestor 100 (FIG. 2) is provided in the biogas removal line 92 to prevent the possible propagation of flame from the biogas burner system 94 back to the biogas storage zone 56 in the reactor 10. The biogas is pressurized slightly by a biogas blower 104, a sufficient amount to overcome the pressure losses in the biogas burner system 94. The initial process in the biogas burner system 94 is combustion in a high efficiency thermal oxidizer 106. The combustion temperature in the thermal oxidizer 106 is continuously monitored and automatically controlled by the instrumentation on the biogas burner system 94. A natural gas or propane source 108 is required for the pilot flame 110 in the thermal oxidizer 106.

In order to make beneficial us of the heat value of the biogas, a heat recovery system 112 is employed to extract heat from the biogas combustion exhaust 114. An air-to-water heat exchanger 116 is located in the exhaust stack 118 from the thermal oxidizer 106 which typically uses a portion of the internal recycle flow to pass through the heat exchanger 116 and then on line 120 to mix with the reactor influent on recycle line 18 thereby to add heat to the reactor contents. An automatic temperature controller 122 located at the influent piping 22, 24 at the inlet of the reactor 10 is used to modulate the control valve 80 to send more or less recycle water via line 124 to the heat exchanger 116 thereby to control the temperature of the water on recycle line 18 to the inlet of the reactor 10. The heat recovery system is equipped with a by-pass exhaust stack 126 to allow the heat exchanger to be by-passed when added heat is not required, or when maintenance is necessary on the heat recovery system 112.

A supplemental/auxiliary heating system 128, consisting of a steam source 132 and injector valve or heat exchanger 130, is also provided to heat the influent flow on recycle line 18 in the event the heating requirements of the reactor 10 cannot be satisfied by the biogas combustion heat recovery system 112 above, and also during start-up of the anaerobic process when biogas production is not adequate to operate the biogas burner system 94.

Excess biological solids (sludge) in the suspended growth zone 34 is removed intermittently via the waste sludge piping 134 for disposal. A waste sludge pump 136 is provided to pump the sludge from the reactor 10 at a controlled rate. The reactor is equipped with a number of sampling ports 138 located at intervals up the side wall of the reactor 10. These ports 138 allow monitoring of the sludge level in the suspended growth zone 34 as well as other process variables at various depths of the reactor 10.

An optimum pH range of 6.5 to 7.2 is needed for effective operation of the BEHAR system. Since most high strength wastewaters are acidic, and alkalinity is consumed during anaerobic treatment, it is normally necessary to supplement the wastewater with alkalinity in order to maintain a proper operating pH range in the reactor. No pH adjustment of the wastewater is made prior to mixing with the recycle flow in order to make beneficial use of the alkalinity and buffering capacity of the recycle stream. A magnesium hydroxide ($Mg(OH)_2$) source 140, sodium hydroxide (NaOH) source 142, and lime ($Ca(OH)_2$) source 144 are available for alkalinity addition to the system. $Mg(OH)_2$ is fed at a preset feed rate in order to provide each of micronutrient magnesium, baseload alkalinity addition, sulfide toxicity control, and biogas $H_2S$ control. The amount of $Mg(OH)_2$ added is predetermined based upon the critical limiting factor (for example, alkalinity, sulfide toxicity control or biogas $H_2S$ control). Since ferric chloride ($FeCl_3$) is acidic and $Mg(OH)_2$ is basic, these chemical additions have to be balanced for sulfide toxicity control based on pH control in the reactor 10. An automatic pH controller is then used to add NaOH or $Ca(OH)_2$ as needed for alkalinity addition for final pH trim control. An additional pH monitoring system is then provided on the recycle line 18 to monitor the pH of the reactor and sound a trouble alarm if the pH of the reactor 10 falls outside the predetermined set points.

Normally, six separate chemical feed systems are provided to feed the sources $Mg(OH)_2$ 140, NaOH 142, lime 144, $FeCl_3$ or $FeCl_2$ 146, macronutrients 148 and micronutrients 150. Six separate controllable pumps 152 through 162 then control the respective feed sources 140 through 150 to supply input to the recycle line 18. As previously described, $Mg(OH)_2$ and NaOH are added to provide alkalinity, magnesium as a micronutrient and for sulfide complexation. $Mg(OH)_2$ is added as the primary alkalinity source under conditions where excessive alkalinity requirements are needed in order to minimize potential for sodium toxicity in the reactor and biogas $H_2S$ control. Lime also provides alkalinity and calcium as a micronutrient. $FeCl_3$ and/or $FeCl_2$ are added as a micronutrient, for odor control, and for sulfide complexation. Both $FeCl_3$ or $FeCl_2$ and $Mg(OH)_2$ are used in combination for sulfide toxicity control by complexing or precipitating sulfides as they are formed in the reactor. $FeCl_3$ and $FeCl_2$ each add acidity to the reactor while $Mg(OH)_2$ adds alkalinity. Sulfate reduction to sulfides also consumes acidity in the reactor. Therefore, it is important to maintain a proper balance between the $Mg(OH)_2$ and $FeCl_2$ or $FeCl_2$ added to the reactor for sulfide toxicity control and optimization/enhancement of the BEHAR process. Soluble sulfide may be added with the alkalinity addition chemicals to precipitate heavy metals.

Both macronutrients (nitrogen and phosphorus) and micronutrients (trace metals) are critical to successful performance of anaerobic treatment systems. Nitrogen and phosphorus levels are normally inadequate in high strength industrial wastewaters. Aqueous ammonia and phosphoric acid can be used to supply nitrogen and phosphorus, as well as various forms of fertilizers. In addition to the nitrogen and phosphorus requirements, facilities are provided to add the following chemicals to ensure adequate micronutrients are available for growth requirements.

Ferric chloride/ferrous chloride
Calcium chloride
Ammonium molybdate
Nickel chloride
Copper sulfate
Cobalt chloride
Zinc sulfate The trace metals are critical in controlling the rate of enzyme reactions which set the rate of biological activity. Trace metals also serve as regulators of osmotic pressure and to transfer electrons in oxidation-reduction reactions such as the storage of energy, i.e., the conversion of ADP to ATP. The major trace elements required by bacteria include iron, magnesium, calcium, copper, zinc, nickel, cobalt, and molybdenum.

In summary, the invention provides a biochemically enhanced anaerobic treatment process coupled with a unique reactor design to offer significant advantages, compared with the prior art, in terms of treatment performance, process optimization, biogas quality, and capabilities to treat complex, inhibitory, and difficult to treat industrial wastewaters. A unique process is also provided for recovering the methane rich biogas as a reactor heat source through heat exchangers in the biogas burner and the effluent recycle stream. Proper use of the vertical flow and crossflow fixed-film media also enhances treatment performance in addition to providing solid/liquid/gas separation for clear treated effluent discharge. A unique combination of $Mg(OH)_2$ and $FeCl_3$ or $FeCl_2$ for micronutrients, sulfide toxicity control, biogas $H_2S$ quality control, and alkalinity and pH control provides capabilities to treat complex industrial wastewaters that could not otherwise be treated anaerobically, to optimize and enhance anaerobic treatment, and to produce high quality biogas without biogas scrubbing and cleaning processes.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. A process for treatment of highly contaminated industrial waste waters, comprising:
   introducing influent wastewater into a lower suspended growth zone of a digestion vessel wherein anaerobic digestion commences;
   receiving up-flow of digestion product through a middle fixed film zone of the digestion vessel to effect solids/liquids/gas separation;
   drawing off waste solids from the floor of the digester vessel at a predetermined rate of removal;
   receiving liquids/gas up-flow through an upper quiescent zone of the digestion vessel;
   drawing off treated effluent from said quiescent zone;
   selecting a portion of treated effluent for conduction via recycle line back to said point of introduction for mixture with said influent wastewater; and
   injecting selected ones of plural process enhancement chemicals in predetermined amounts into said recycle line, which plurality includes preselected amounts of $Mg(OH)_2$ and iron chloride to effect cleaning of the biogas.

2. The process of claim 1 which is further characterized to include:

collecting gas from the liquids/gas up-flow through the upper quiescent zone and igniting the gas to produce heat; and introducing controlled amounts of heat into the recycle line.

3. The process of claim 2 wherein:

the temperature of operation within the digester vessel may simulate both mesophilic conditions and thermophilic conditions.

4. The process of claim 1 which includes the further step of:

adding additional $FeCl_2/FeCl_3$ for odor control of biogas hydrogen sulfide.

5. The process of claim 1 wherein:

bulk liquid sulfide toxicity control is effected by adjusting the amounts of $Mg(OH)_2$ and $FeCl_2/FeCl_3$ to maintain the bulk liquid soluble sulfides at below 200 milligrams per liter.

6. The process of claim 1 wherein the step of injecting includes:

adding predetermined amounts of soluble sulfides and alkalinity addition chemicals to precipitate heavy metals and provide heavy metal toxicity control.

7. The process of claim 1 which is further characterized to include:

adjusting the ratio of effluent recycle liquid to influent wastewater through the digester vessel to effect alkalinity and buffering control.

8. The process of claim 1 wherein:

the plural enhancing chemicals are primarily $Mg(OH)_2$ in such concentration to control pH, alkalinity and buffering capacity, to control sulfide toxicity, and to reduce $H_2S$ by biogas cleaning.

9. Apparatus for treating wastewater, comprising:

an anaerobic digester vessel having a floor and roof, and having a lower suspended growth zone, a middle fixed film zone, and an upper quiescent zone that includes a liquid level and an uppermost gas storage zone;

means introducing influent wastewater into a lower suspended growth zone for digestion commencement;

filter media supported in the middle fixed film zone receiving up-flow of digestion product for release of liquid/gas upward into the upper quiescent zone;

means for drawing off waste solids from the lowermost region of the digester vessel for conduction to disposal;

conduit means for drawing off treated effluent from said upper quiescent zone;

a recycle line connected to said conduit means for conducting a selected amount of treated effluent back to said means introducing influent wastewater; and a plurality of chemical reservoirs with injection pumps connected for input to said recycle line, selected ones of the chemical reservoirs containing $Mg(OH)_2$ and iron chloride for injection in preselected amounts to effect cleaning of the biogas.

10. Apparatus as set forth in claim 9 which is further characterized to include:

a source of steam including a controllable valve connected for selective injection of steam into said recycle line.

11. Apparatus as set forth in claim 9 wherein said means introducing comprises:

a network of perforate distributor pipes which spread the influent relatively evenly over the entire area of the digester vessel.

12. Apparatus as set forth in claim 9 wherein said filter media comprises:

a lower portion of vertical flow corrugated sheet; and an upper portion of crossflow corrugated sheet.

13. Apparatus as set forth in claim 9 wherein said conduit means comprises:

a collection pipe network spread across the entire area of the digester vessel beneath the liquid level in the quiescent zone; and at least one gas vent pipe extending from the pipe network upward to terminate above the liquid level.

14. Apparatus as set forth in claim 13 which is further characterized to include:

a first effluent control chamber closed to the atmosphere disposed at digester liquid level;

a first conduit connecting between said conduit means and the bottom of said effluent control chamber to provide a liquid seal preventing biogas escape into the atmosphere;

a second effluent control chamber adjacent to and in liquid communication with said first effluent control chamber but open to the atmosphere and having an adjustable weir to control and maintain liquid level within the digester vessel; and a third effluent control chamber adjacent the adjustable weir for conducting out all liquid overflow as treated effluent.

15. Apparatus as set forth in claim 14 which is further characterized to include:

means for spraying down upon the liquid surface within the digester vessel to effect breakup of surface congelation;

a conduit connected between the recycle line and said means for spraying; and a buoyant skimmer floating on the liquid surface and carrying foam/scum for deposit through said effluent chambers to treated effluent disposal.

16. Apparatus as set forth in claim 9 which is further characterized to include:

a biogas burner system;

a gas conduit connecting combustible gas output from said uppermost gas storage zone to said burner system;

means for conducting a selectable portion of said recycle line through said burner system for heat exchange.

17. Apparatus as set forth in claim 16 which is further characterized to include:

a temperature controller sensing the temperature at point of introduction of influent and adjusting said biogas burner system for selected change in temperature of said recycle line.

18. Apparatus as set forth in claim 9 wherein:

there are six of said chemical reservoirs containing magnesium hydroxide, caustic soda, iron chloride, lime, micronutrient and macronutrient.

* * * * *

UNITED STATES PATENT AND TRADEMARK OFFICE
CERTIFICATE OF CORRECTION

PATENT NO. : 5,228,995
DATED : July 20, 1993
INVENTOR(S) : Enos L. Stover

It is certified that error appears in the above-indentified patent and that said Letters Patent is hereby corrected as shown below:

Column 5, line 50, delete the formula and substitute the formula -- $H_2S \leftrightarrow HS^- + H^+$ -- therefor;

Column 7, line 52, delete "$S_c$" and substitute --$S_e$-- therefor;

Column 8, line 16, delete "$S_c$" and substitute --$S_e$-- therefor;

Column 11, line 53, delete "$FeCl_2$" and substitute --$FeCl_3$-- therefor; and

Column 13, line 8 (line 3 of claim 3), insert --selectively-- after "simulate".

Signed and Sealed this

Twenty-ninth Day of March, 1994

*Attest:*

BRUCE LEHMAN

*Attesting Officer*     *Commissioner of Patents and Trademarks*